(12) United States Patent
Barron et al.

(10) Patent No.: US 7,695,454 B2
(45) Date of Patent: Apr. 13, 2010

(54) FIXED DOSE MEDICATION DISPENSING DEVICE

(75) Inventors: Traci Jo Barron, Chicago, IL (US); Andrew Christopher Burroughs, Kenosha, WI (US); David William Hixson, Longmont, CO (US)

(73) Assignee: Eli Lilly and Company, Indianapolis, IN (US)

( * ) Notice: Subject to any disclaimer, the term of this patent is extended or adjusted under 35 U.S.C. 154(b) by 173 days.

(21) Appl. No.: 10/575,502

(22) PCT Filed: Oct. 15, 2004

(86) PCT No.: PCT/US2004/032304

§ 371 (c)(1),
(2), (4) Date: Apr. 11, 2006

(87) PCT Pub. No.: WO2005/039676

PCT Pub. Date: May 6, 2005

(65) Prior Publication Data

US 2007/0088288 A1    Apr. 19, 2007

(51) Int. Cl.
*A61M 5/00*    (2006.01)

(52) U.S. Cl. ........................ 604/207; 604/187
(58) Field of Classification Search ............... 604/207, 604/187, 153, 211, 209, 210, 181, 208
See application file for complete search history.

(56) References Cited

U.S. PATENT DOCUMENTS

| | | | |
|---|---|---|---|
| 4,475,905 A | 10/1984 | Himmelstrup | |
| 4,832,694 A | 5/1989 | Raphael, III et al. | |
| 5,279,585 A * | 1/1994 | Balkwill | 604/207 |
| 5,279,586 A * | 1/1994 | Balkwill | 604/207 |
| 5,318,544 A | 6/1994 | Drypen et al. | |
| 5,505,704 A | 4/1996 | Pawelka et al. | |
| 5,674,204 A * | 10/1997 | Chanoch | 604/211 |
| 5,961,495 A * | 10/1999 | Walters et al. | 604/208 |

(Continued)

FOREIGN PATENT DOCUMENTS

EP    0 554 996 B1    10/1996

(Continued)

*Primary Examiner*—Kevin C Sirmons
*Assistant Examiner*—Michael J Anderson
(74) *Attorney, Agent, or Firm*—Edward J. Prein (57) ABSTRACT

A guide and follower cooperate to promote a user moving the driver relative to the housing along a travel path that operates the apparatus. The cooperating elements of the nut and the driver are disengaged when the driver is disposed in a reset segment of the travel path, and the cooperating elements of the nut and the driver become engaged when the driver is shifted through a nut engaging segment of the travel path from the reset segment to a nut rotating segment of the travel path. The engagement of the cooperating elements of the nut and the driver cause the nut to screw proximally along the threaded shaft of the drive member when the driver is shifted through the nut rotating segment from the nut engaging segment to an injecting section of the travel path. When the driver is shifted through the injecting section from the nut rotating segment to the reset segment, the nut and the drive member are shifted in the distal direction to axially advance a fluid container piston to dispense medicine, and the cooperating elements of the nut and the driver become disengaged.

7 Claims, 9 Drawing Sheets

U.S. PATENT DOCUMENTS

| | | | |
|---|---|---|---|
| 6,001,089 A * | 12/1999 | Burroughs et al. | 604/506 |
| 6,096,010 A * | 8/2000 | Walters et al. | 604/207 |
| 6,110,152 A * | 8/2000 | Kovelman | 604/232 |
| 6,221,046 B1 | 4/2001 | Burroughs et al. | |
| 6,562,006 B1 | 5/2003 | Hjertman et al. | |
| 6,663,602 B2 * | 12/2003 | Møller | 604/211 |
| 6,827,708 B2 * | 12/2004 | Kirchhofer | 604/187 |
| 6,899,699 B2 * | 5/2005 | Enggaard | 604/246 |
| 6,936,032 B1 * | 8/2005 | Bush et al. | 604/187 |
| 2004/0097883 A1 * | 5/2004 | Roe | 604/207 |
| 2007/0088288 A1 * | 4/2007 | Barron et al. | 604/207 |

FOREIGN PATENT DOCUMENTS

| | | |
|---|---|---|
| WO | WO 02/30495 A2 | 4/2002 |
| WO | WO 02/092153 A2 | 11/2002 |

\* cited by examiner

FIXED DOSE MEDICATION DISPENSING DEVICE

BACKGROUND OF THE INVENTION

The present invention relates generally to medication dispensing devices, and, in particular, to a device that facilitates dispensing a fixed dose of a liquid medication.

Patients suffering from a number of different diseases frequently must inject themselves with medication. To allow a person to conveniently and accurately self-administer medicine, a variety of devices broadly known as injector pens or injection pens have been developed. Generally, these pens are equipped with a cartridge including a piston and containing a multi-dose quantity of liquid medication. A drive member, extending from within a base of the injector pen and operably connected with typically more rearward mechanisms of the pen that control drive member motion, is movable forward to advance the piston in the cartridge in such a manner to dispense the contained medication from an outlet at the opposite cartridge end, typically through a needle that penetrates a stopper at that opposite end. In disposable or prefilled pens, after a pen has been utilized to exhaust the supply of medication within the cartridge, a user, who then begins using a new replacement pen, discards the entire pen. In reusable pens, after a pen has been utilized to exhaust the supply of medication within the cartridge, the pen is disassembled to allow replacement of the spent cartridge with a fresh cartridge, and then the pen is reassembled for its subsequent use.

One known injection pen used to administer a fixed dose of medication is disclosed in PCT Publication Number WO 02/30495. Although this injection pen, and perhaps other devices known in the art, may be suitable to deliver a fixed dose, it would be desirable to provide an injection pen that is even simpler to operate to properly deliver a fixed dose of medication.

SUMMARY OF THE INVENTION

In one form thereof, the present invention provides a medication dispensing apparatus including a housing, an axially extending drive member rotatably and axially fixed within the housing during dose preparing, and rotatably fixed and axially movable in a distal direction relative to the housing during dose injecting, the drive member including a threaded shaft, a fluid container defining a medicine-filled reservoir with a movable piston at one end and an outlet at the other end, the piston being engagable by the drive member to be advanced toward the outlet when the drive member is moved distally, a nut threadedly engaged with the drive member shaft to be axially movable relative thereto during rotation of the nut relative to the drive member, and a nut driver rotatably and axially shiftable relative to the housing. The nut and the driver include cooperating elements which when engaged rotatably lock together the nut and the driver, and which when disengaged permit relative rotation of the nut and the driver. The apparatus also includes a guide disposed on one of the driver and the housing, a follower disposed on the other of the driver and the housing, wherein the guide and follower cooperate to promote a user moving the driver relative to the housing along a travel path that operates the apparatus, which travel path includes a dose preparing section and a dose injecting section, which dose preparing section includes a reset segment, a nut engaging segment, and a nut rotating segment connected in sequence, and wherein the injecting section connects the nut rotating segment with the reset segment. The cooperating elements of the nut and the driver are disengaged when the driver is disposed in the reset segment, and the cooperating elements of the nut and the driver become engaged when the driver is shifted through the nut engaging segment from the reset segment to the nut rotating segment. The engagement of the cooperating elements of the nut and the driver cause the nut to screw proximally along the threaded shaft when the driver is shifted through the nut rotating segment from the nut engaging segment to the injecting section. When the driver is shifted through the injecting section from the nut rotating segment to the reset segment, the nut and the drive member are shifted in the distal direction to axially advance the fluid container piston to dispense medicine from the outlet, and the cooperating elements of the nut and the driver become disengaged. The guide includes a hard stop for the follower to define an end of the reset segment of the driver travel path, and the hard stop when abutted by the follower rotationally aligns the driver with the nut engaging segment of the travel path.

One advantage of the present invention is that a medication dispensing apparatus may be provided which is simple to operate correctly to deliver the same, predetermined dose of medication each and every time used.

Another advantage of the present invention is that a medication dispensing apparatus may be provided which includes elements to interfere with certain improper operations of the pen.

Still another advantage of the present invention is that a medication dispensing apparatus may be provided which facilitates a sequencing through the cycle of steps necessary to prepare and deliver a dose of medication.

BRIEF DESCRIPTION OF THE DRAWINGS

The above-mentioned and other advantages and objects of this invention, and the manner of attaining them, will become more apparent, and the invention itself will be better understood by reference to the following description of embodiments of the invention taking in conjunction with the accompanying drawings, wherein:

FIG. 11 a is a front view of the proximal end of the apparatus when arranged as shown in FIG. 11.

Corresponding reference characters indicate corresponding parts throughout the several views. Although the drawings represent an embodiment of the present invention, the drawings are not necessarily to scale, and certain features may be exaggerated or omitted in some of the drawings in order to better illustrate and explain the present invention.

DETAILED DESCRIPTION OF THE INVENTION

Figure 1:
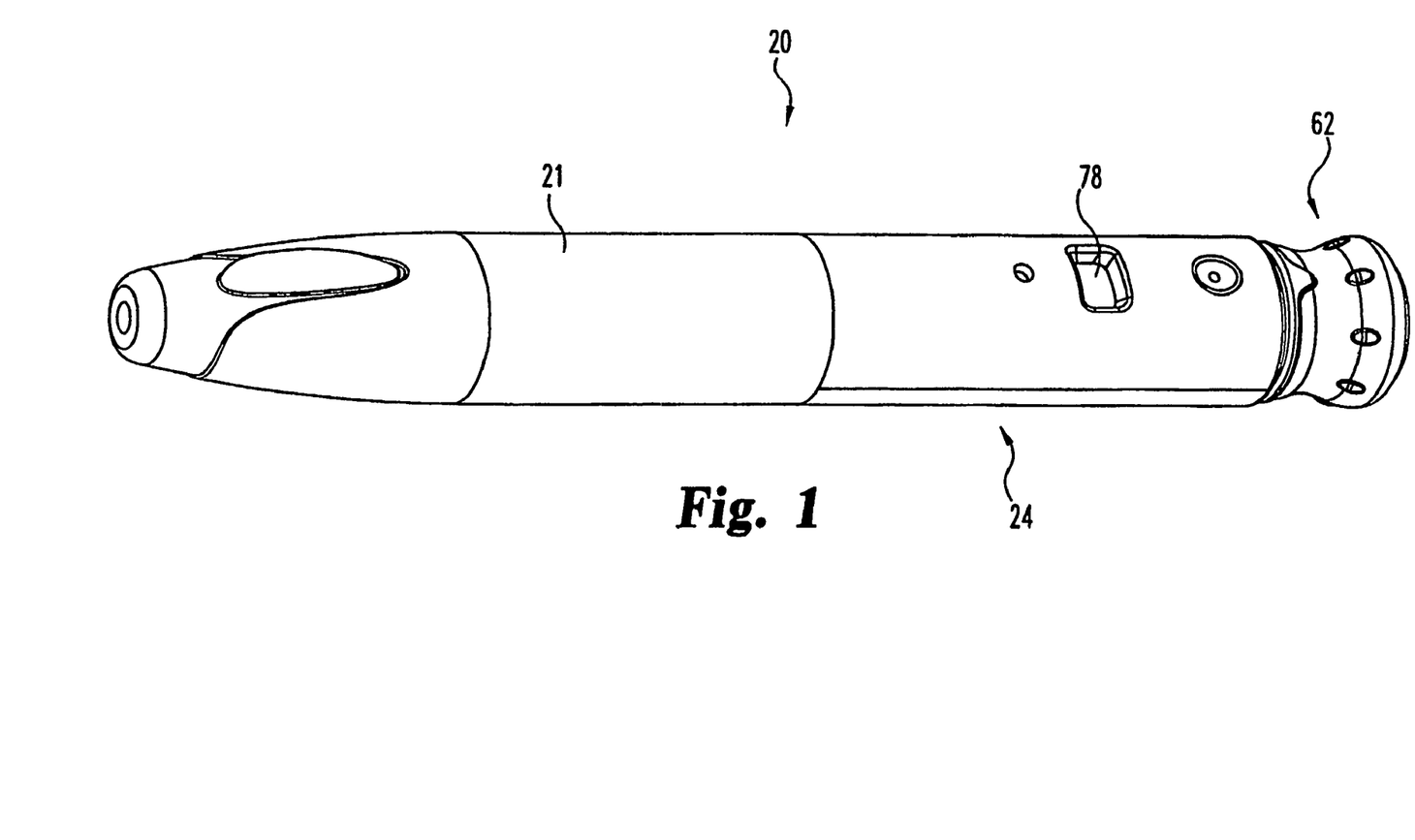
FIG. 1 is a perspective view of one embodiment of a medication dispensing apparatus in accordance with the present invention.
Figure 2:
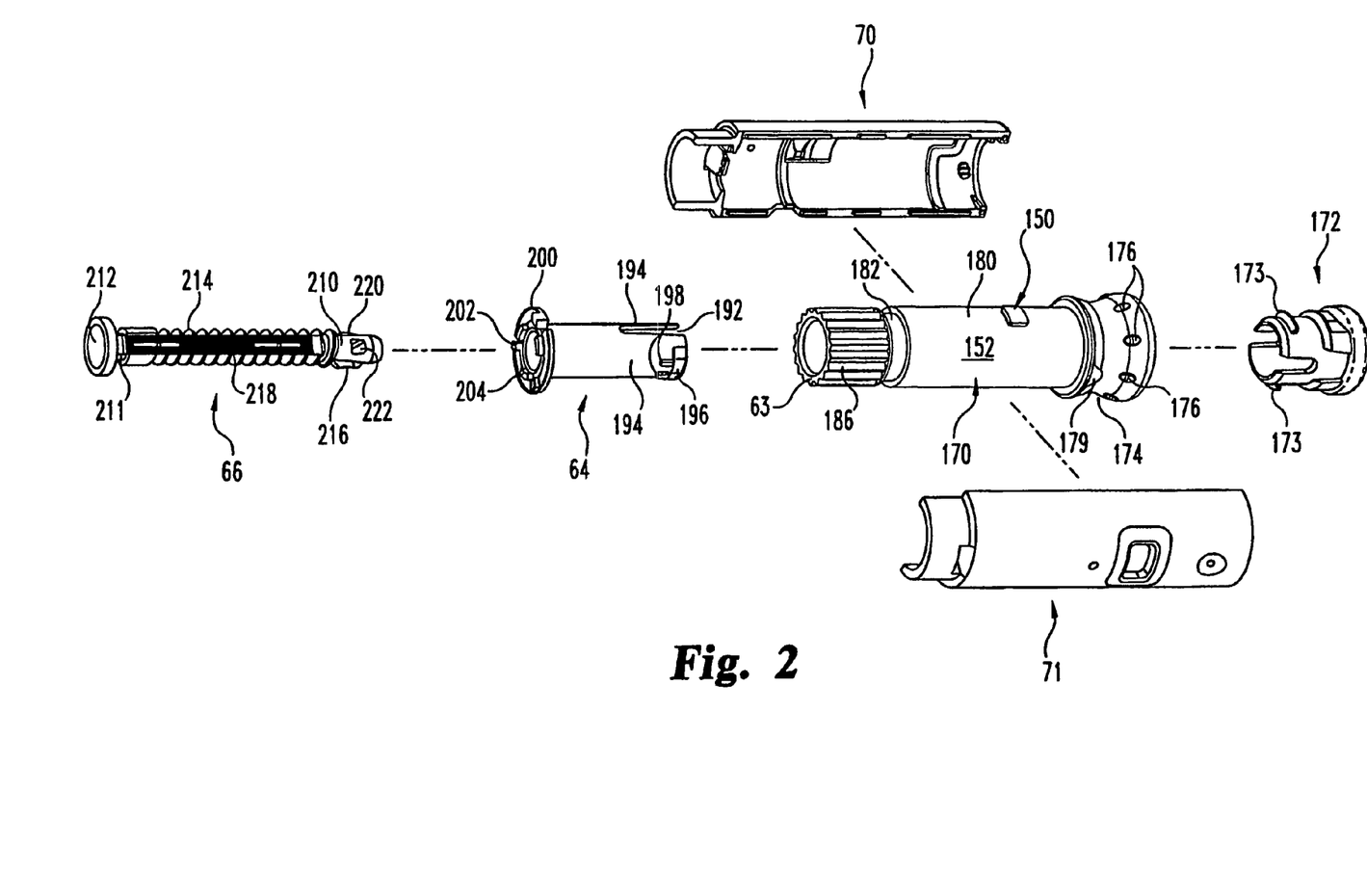
FIG. 2 is an exploded perspective view of portions of the apparatus of FIG. 1.
Figure 3:
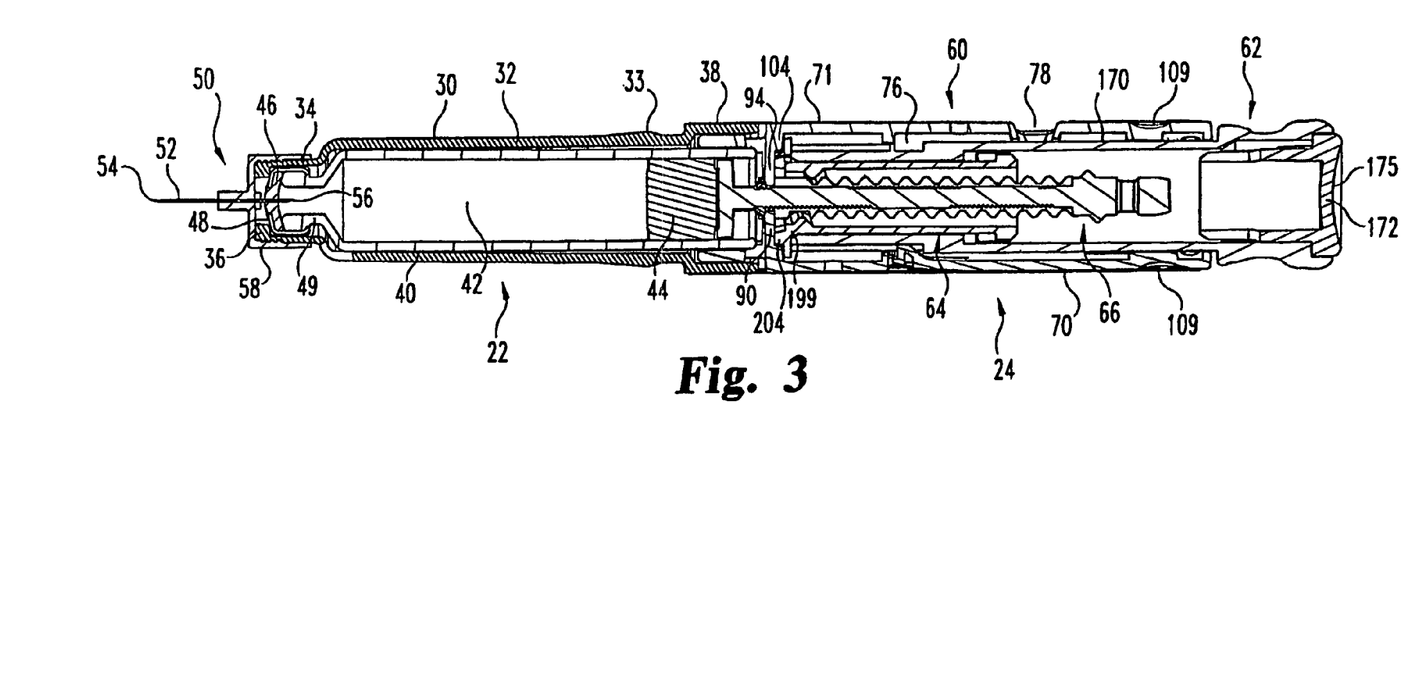
FIG. 3 is a longitudinal sectional view of the apparatus of FIG. 1, wherein the apparatus is shown without a cap and with a pen needle assembly attached at its distal end.

Referring now to FIGS. 1-3, there is shown a first embodiment of a medication dispensing apparatus of the present invention. Any directional references in this detailed description with respect to FIG. 1 or any of the other Figures, such as right or left, are intended for convenience of description, and by itself does not limit the present invention or any of its components to any particular positional or spatial orientation.

The apparatus, generally designated 20, is shown as an injector pen, which pen has an elongated, substantially writing instrument-like form, although other forms are within the scope of the invention. Injector pen 20 is conceptually similar in many respects to the devices disclosed in U.S. Pat. Nos. 5,938,642, 6,001,089 and 6,221,046, and PCT Publication Number WO 02/30495, the disclosures of all of which are incorporated herein by reference to facilitate an understanding of the invention.

Medication injector pen 20 is a disposable or prefilled pen, in that after the quantity of medicine contained therein is exhausted by multiple operations of the pen, the entire pen is discarded rather than being reset and reloaded with a replacement container of medicine. Pen 20 is operable by a user to inject a predetermined dose of medication, such as may be appropriate with some therapeutics loaded therein by the manufacturer. For example, an injectable formulation containing glucagon-like peptide-1(7-37) including analogs and derivatives thereof, as well as exendin-4 and analogs and derivatives thereof, used to treat diabetes may be well suited for the apparatus of the present invention.

Injector pen 20 generally includes a distal portion 22 and a proximal portion 24. Distal portion 22 contains the medicinal fluid to be outlet at its distal end upon pen operation, and this portion is shown received within pen cap 21 in FIG. 1. Proximal portion 24 contains the injecting mechanism used to force the contained medicine from the needled end.

Distal portion 22 includes a retainer 30 with a cartridge 40 held therein. Cartridge retainer 30 is shown formed with a one-piece construction out of a transparent plastic to allow the cartridge contents to be visible. Retainer 30 includes a barrel portion 32 and a stepped down neck portion 34. An annular end face 36 forms the distal end of portion 34. Barrel portion 32 includes an interior hollow sized to accommodate a cartridge. The exterior of barrel portion 32 near its proximal end is formed with a detent, such as a circumferential rib 33, that cooperates with the pen cap configuration to allow a removable snap-mounting of pen cap 21 to retainer 30.

Cartridge 40 is of conventional design and defines a medicine-filled reservoir 42 that is closed at its proximal end by a piston 44 that is axially slidably and sealably engaged with the cartridge interior wall to hold the fluid medication within reservoir 42. The distal, outlet end of cartridge reservoir 42 is sealed by a septum 46 held by a cap 48 that is secured to a stepped-down diameter neck portion 49 of the cartridge.

A pen-needle assembly 50 of known design is shown in FIG. 3 mounted to apparatus 20 and includes a double-ended needle cannula or injection needle 52 having a distal tip 54 at one end and a proximal point 56 at the other. Injection needle 52 is mounted in a tubular hub 58 that is structured, such as via internal threading, to cooperate with external threads on the neck portion 34 so as to be removably mounted to the retainer distal end. A not shown needle cap mounted to the hub, which needle cap is removed when pen 20 is used to inject medicine, may protect tip 54. Although the needle assembly is shown as having a single injection needle, needle assemblies which may be used with pen 20 may be of various types known in the art, including, but not limited to, assemblies with one or more shortened injection needles, including microneedle arrays.

When pen-needle assembly 50 is mounted on retainer 30 as shown in FIG. 3, the proximal point 56 of injection needle 52 passes through a central opening in the annular end face 36, an opening in cap 48, and penetrates cartridge septum 46 to provide a fluid flow outlet by which medicine within cartridge reservoir 42 can be dispensed from needle tip 54 during operations of injector pen 20.

In embodiments in which a smaller volume cartridge than shown is to be used, such as a smaller diameter cartridge having a similar overall length, the interior of barrel 32 may be formed with a plurality of angularly spaced, radially inwardly projecting ribs, such as four ribs spaced 90° apart, that longitudinally extend the length of the barrel and which center the smaller diameter cartridge therein. Such ribs also exist in a radially shorter form in the barrel portion that accommodates cartridge 40 as described above to allow an opening of the draft of the retainer 30.

The fluid medicine container shown in FIGS. 1-3 and described above is illustrative and not intended to be limiting as other constructions may be employed within the scope of the invention. For example, rather than the shown container in which a distinct cartridge is held within a one-piece retainer, the cartridge could be constructed to be sufficiently durable and adapted to secure directly to a pen proximal portion 24 without any protective retainer there around, and with the pen-needle assembly directly mountable to the cartridge.

Proximal portion 24 of injector pen 20 includes an external, protective housing, generally designated 60, a nut driver, generally designated 62, a nut 64, and a screw element 66. With additional reference to FIG. 5, housing 60 is shown formed in two parts from a lightweight material, such as injection molded plastic. The housing parts are shown as longitudinal shell halves 70 and 71 that are secured together during manufacture in a known fashion, such as via ultrasonic welding. For example, male weld joints 73a of part 70 insert within female weld joints 73b of part 71. A pair of recesses 74 in housing part 70 which accommodate pins 75 on part 71, as well as several ribs that fit in complementary recesses on the housing part edges, serve to align the shell halves during manufacturing assembly. Housing parts 70 and 71 when assembled form a housing body that defines an internal hollow 76 in which screw element 66 extends in an axial or longitudinal direction. A window 78 in the housing part 71 is shown. Window 78 allows visual cues located on the exterior surface of nut driver 62 to be visible, which cues faciliate pen operation as described further below. Window 78 may be provided with a magnifying lens if desired to make the cues on the nut driver even more visible.

The distal ends of shell halves 70 and 71 are stepped down to form collar portions 82 and 84 respectively, which collar portions 82 and 84 are sized to receive thereover the radially enlarged sleeve portion 38 of retainer 30. Sleeve portion 38 is fixedly mounted or secured to collar portions 82, 84 in a known fashion, such as via an ultraviolet cured adhesive that also serves to secure the shell halves 70 and 71, during pen assembly by the manufacturer. During this retainer mounting, the cartridge 40 is caused to be axially constrained directly between the interior surface of retainer annular face 36 and a portion of the housing. In the shown embodiment, such constraining housing portion is rib 88 that is integrally formed with, and axially projects distally from, a transversely extending, annular shoulder 90 of housing part 70, as well as a similar rib 92 on a similar shoulder 94 of housing part 71. Ribs 88 and 92 are oriented approximately 180° apart when the housing parts are assembled to abut diametrically opposed end portions of the cartridge.

Integrally formed with shoulder 90 is a radially inwardly projecting flange 96 from which distally projects one or more, such as a pair of, resilient pawls or tangs 98. Tangs 98 and flange 96 are used to prevent axial proximal movement (i.e. backup) and rotational movement of the screw element 66 relative to the housing 60. Shoulder 94 similarly includes flange 100 and tangs 102. The tangs on each housing part are axially staggered so as to engage successive ratchet teeth described below. The anti-backup feature prevents screw element 66 from moving proximally during pen use, such as during either dose preparing or dose injecting. Other types of anti-backup and anti-rotation mechanisms may be employed within the scope of the invention.

The proximal face of shoulders 90 and 94 each include a series of three upstanding, ramp shaped ribs 104. Ribs 104 are cooperatively designed with nut 64 to prevent inadvertent nut rotation when the nut is not rotationally locked with the driver 62.

Transverse ribs 106 and 108 on parts 70 and 71, respectively, aid in centering nut driver 62 within the housing. Other shown aspects of the housing associated with manufacture and assembly include inwardly projecting ejector steps 105 that receive ejection pins when the housing parts are forced from their molds during manufacture, openings 107 that are used during assembling of the housing parts together, concavities 109 shown in FIG. 3 which are gate recesses where plastic is injected into the mold during manufacture, and ear 111 that is formed integrally with rib 122 and which provides a sufficiently thick area of plastic to gate into.

Housing part 70 also includes a U-shaped groove formed therein to define a flexible leg 110 having an inwardly extending finger 112 at the end thereof. Finger 112 includes a proximal, tapered or ramping surface 114 that terminates in a flat 116 having a distal face 118 which is transversely oriented.

Figure 5:
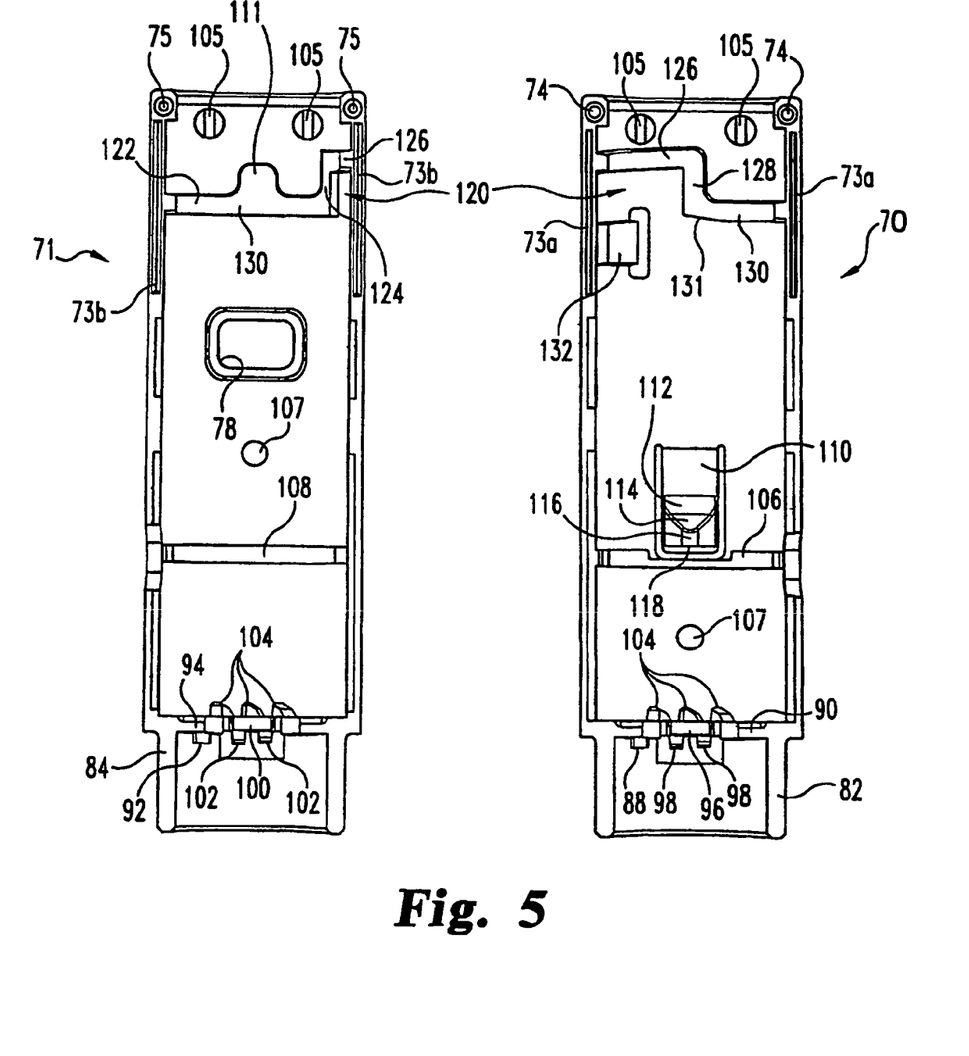
FIG. 5 is a front view of the two-part housing of the apparatus of FIG. 1, wherein one of the housing parts has been rotated open by 180° to reveal the interior hollows of the housing parts.
Figure 6:
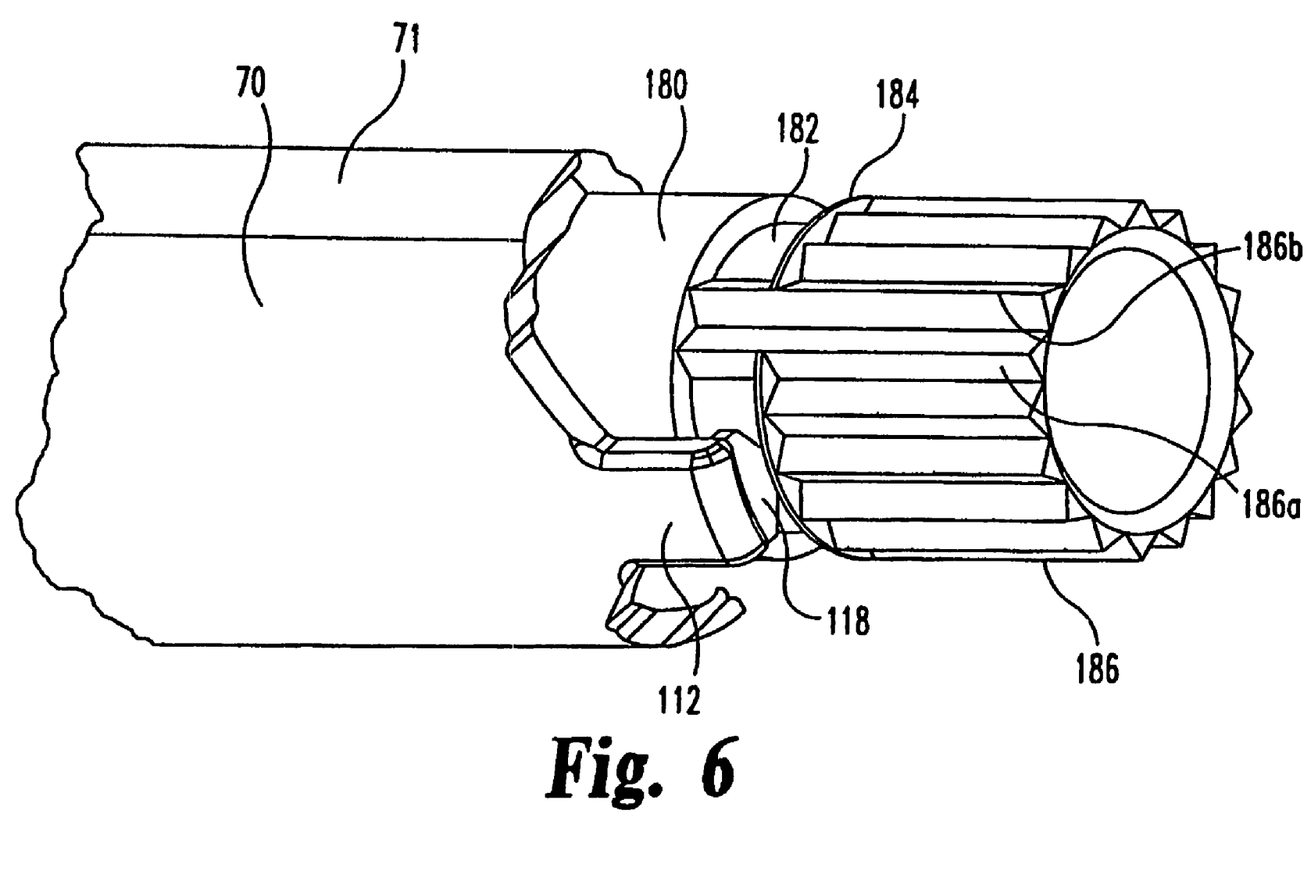
FIG. 6 is a partial perspective view, in partial cutaway, of the housing and nut driver, particularly showing a unit click finger prior to having reached the zeroing position.

With reference to FIG. 5, as well as FIGS. 7-11, the proximal region of housing 60 includes guide features on its interior surface that cooperate with a follower on the exterior surface of the nut driver 62 to facilitate or promote proper operation of the driver and thereby pen 20. The guide, generally designated 120, includes a circumferentially extending, radially inwardly projecting rib 122 that includes first portion 124, second portion 126, third portion 128 and fourth portion 130. First portion 124 is straight and longitudinally oriented. Second portion 126 has a first end 126a that extends from the proximal end 124b of first portion 124. Second portion 126 is pitched relative to the pen longitudinal axis so as to be helically oriented to continue slightly proximally along its length from end 126a. Fourth portion 130 is positioned distally of second portion 126, and has an end 130b that ends at distal end 124a of first portion 124. Fourth portion 130 extends from first portion 124 in an opposite angular direction as second portion 126 extends from first portion 124, and is straight and oriented generally transverse to the axis of pen 20. Third portion 128 is straight and longitudinally oriented, has a longer axial length than first portion 124, and has a proximal end 128a that terminates at the end 126b of second portion 126, and a distal end 128b that terminates at an end 130a of fourth portion 130 so as to directly connect guide rib portions 126 and 130. A slight angling 131 at the end of 130 serves as a lead-in to limit follower snagging and to aid in forcing the nut and screw distally. Second portion 126 and fourth portion 130 each include small chamfers at the intersections of housing parts 71 and 72 to eliminate follower snagging in the event that the parts are slightly misaligned during assembly.

Guide 120 further includes a radially inwardly projecting element 132 particularly designed both to further promote proper pen operation, and to serve as a positive or physical stop to address certain modes of possible pen misuse. Although shown as a single, solid molded element, the guide element could be differently configured, such as a thinner, multi-angled rib.

Guide element 132 includes a first face 134 which is straight, a second face 136 which is on pitch, and a third face 138 which is straight. Due to the axial length of the follower, first face 134 defines with the right surface of rib portion 124 a channel 140 therebetween for directing follower travel. Guide second face 136 is distal of and parallel to the facing surface of rib portion 126, and together with such facing surface defines channel 142 therebetween. Due to the axial length of the follower, third face 138 and defines with the left surface of rib portion 128 a channel 144 therebetween for follower travel. Guide faces 134 and 138 are longitudinally arranged and therefore are parallel with each other as well as with the rib portion surfaces with which they form channels.

A follower, generally designated 150, radially outwardly projects from the exterior surface 152 of nut driver 62 to interact with guide 120. Follower 150 is shown as being retangular in overall shape with planer surfaces 154, 156, 158 and 160. Follower 150 and guide 120 are complementarily sized and shaped to fit so as to limit the undesired play or movement therebetween while not preventing relative sliding motion. Follower 150 is not radially retractable during pen use, such as during either dose preparing or dose injecting. Although the rib portions and faces of guide 120 are without interruption and therefore continuous, it will be appreciated that such aspects may be continuous as to follower control even with small interruptions therein, provided such interruptations do not permit undesired passage of the follower therethrough.

The travel path of the nut driver 62 relative to the housing 60 is guided by the follower 150 and guide 120. The travel path includes a dose preparing section in which the pen nut driver is manipulated to prepare the pen to dispense its intended dose, and an injection section in which the pen nut driver is manipulated to actually dispense the intended dose after such dose has been prepared.

The injection section of the travel path corresponds to follower 150 distally traveling completely through channel 144. The dose preparing section of the travel path includes a reset segment, a nut-engaging segment, and a nut-rotating segment. The reset segment corresponds to follower 150 traveling along guide rib 130 from the radial or angular position the follower occupies after exiting channel 144 and completing an injection, until reaching the entry of channel 140. The nut-engaging segment of the travel path corresponds to follower 150 proximally traveling completely through channel 140 to reach the entry of channel 142. And, the nut-rotating segment of the travel path corresponds to follower 150 traveling completely through channel 142 to reach the entry of channel 144.

Figure 4:
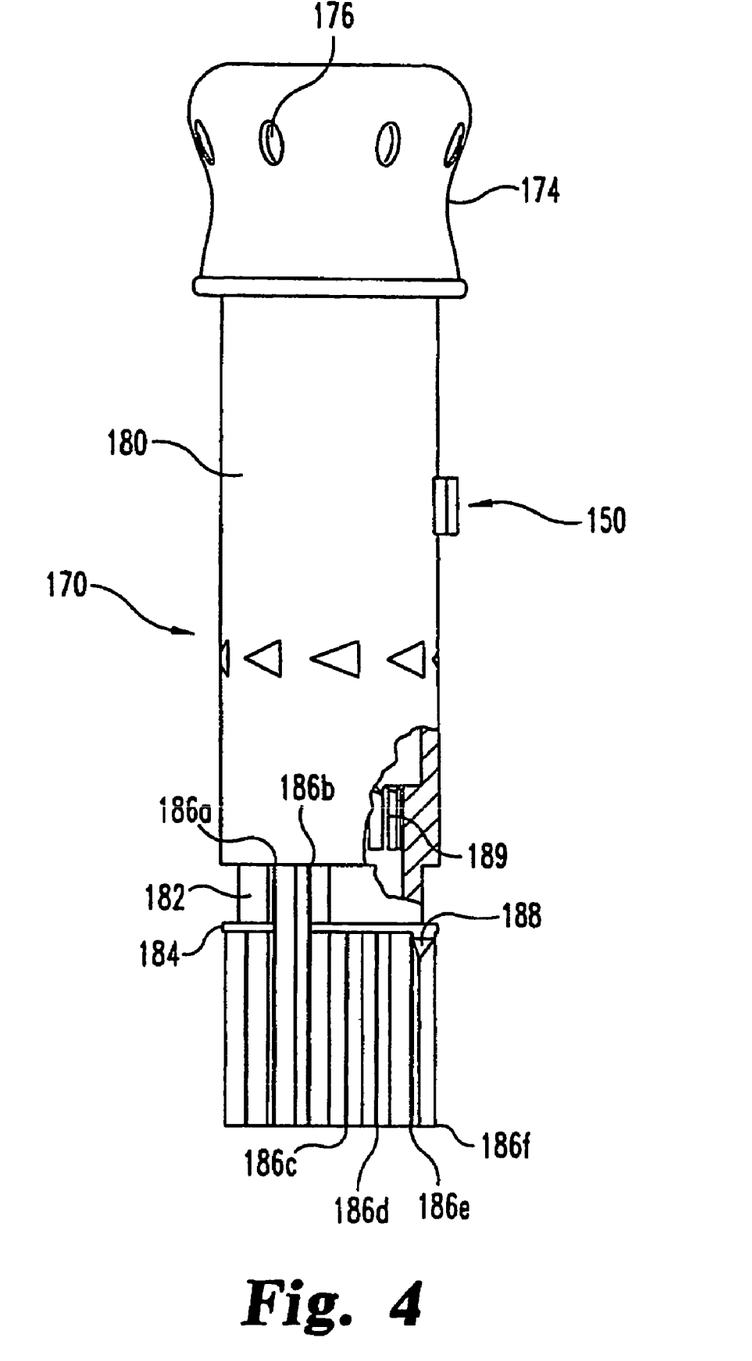
FIG. 4 is a front view of the nut driver of FIG. 2 in partial cutaway to reveal a series of internal splines.

With reference to FIGS. 2 and 3 and 4, nut driver 62 is shown formed in two parts from a lightweight material, such as injection molded plastic. The nut driver parts include a tubular main body 170 with a plug 172 that fills the proximal end of that main body. In the shown embodiment, plug 172 inserts in and is secured into main body 170 during assembly, such as via a pair of lipped prongs 173 that snap lock into not shown, complementary recesses within the interior surface of main body 170.

Although shown as having a two-piece construction which facilitates manufacture, the nut driver may be formed as a single part or as even additional parts assembled together. Driver main body 170 is generally cylindrical in shape and is hollow throughout its axial length. Main body 170 includes a grip portion 174 having a larger diameter and extending proximally of housing 60. Grip portion 174 is externally accessible to be manually rotated and pulled by a user for dose preparing purposes. The interior of grip portion of 170 includes a plurality of closely spaced, axially extending ribs, which ribs do not prevent insertion of plug 172, but which, during the manufacturing process, prevent other similar main body parts in a hopper that feeds the assembly align from improperly nesting therein. Grip portion 174 is shown as having a hourglass-like external profile with a series of angularly spaced, radially protruding ribs 176 so as to be readily graspable by a user, such as between the thumb and fingers of a user, when rotated or pulled to the right from the perspective of a viewer of FIG. 1. Other graspable grip portion configurations may be substituted. The concave, proximal face 175 of plug 172 serves as a push surface against which a force can be applied manually to push the driver during the actual dispensing. Grip portion 174 also includes an alignment aid in the form of a small projection 179 which aligns with the pen window 78 when the nut driver is disposed in the "zero-dose" radial or angular position.

A cylindrical portion 180 of main body 170 extends distally from grip portion 174 and fits within the interior hollow of housing 60. The exterior surface of body portion 180 includes follower 150. The exterior of main body portion 180 further is provided with user cues, not shown in FIG. 2 but shown in FIG. 4, that ring the body portion and that are visible through housing window 78. The user cues provide instructions as to proper pen use, such as a series of directional arrows as further described below.

As further shown in FIG. 4, the region of main body 170 distal of portion 180 includes in sequence a reduced diameter portion forming a circumferential groove 182, a circumferential flange 184 that defines the distal end of groove 182, and a series of elongated splines 186 axially extending externally about the circumference of the distal end of body 170. Two of the splines 186 indicated at 186a and 186b extend axially through an opening in flange 184 and axially span groove 182. A ramp 188 up to the outer edge of flange 184 is molded into the proximal end of the V-shaped channel formed by splines 186e and 186f. Splines 186c and 186d are of slightly lesser diameter than the other splines 186 so as to offer less resistance to sliding under finger 112 during use. All of the splines 186 other than 186a-f merely aid in centering main body 170 within housing 60.

Figure 12:
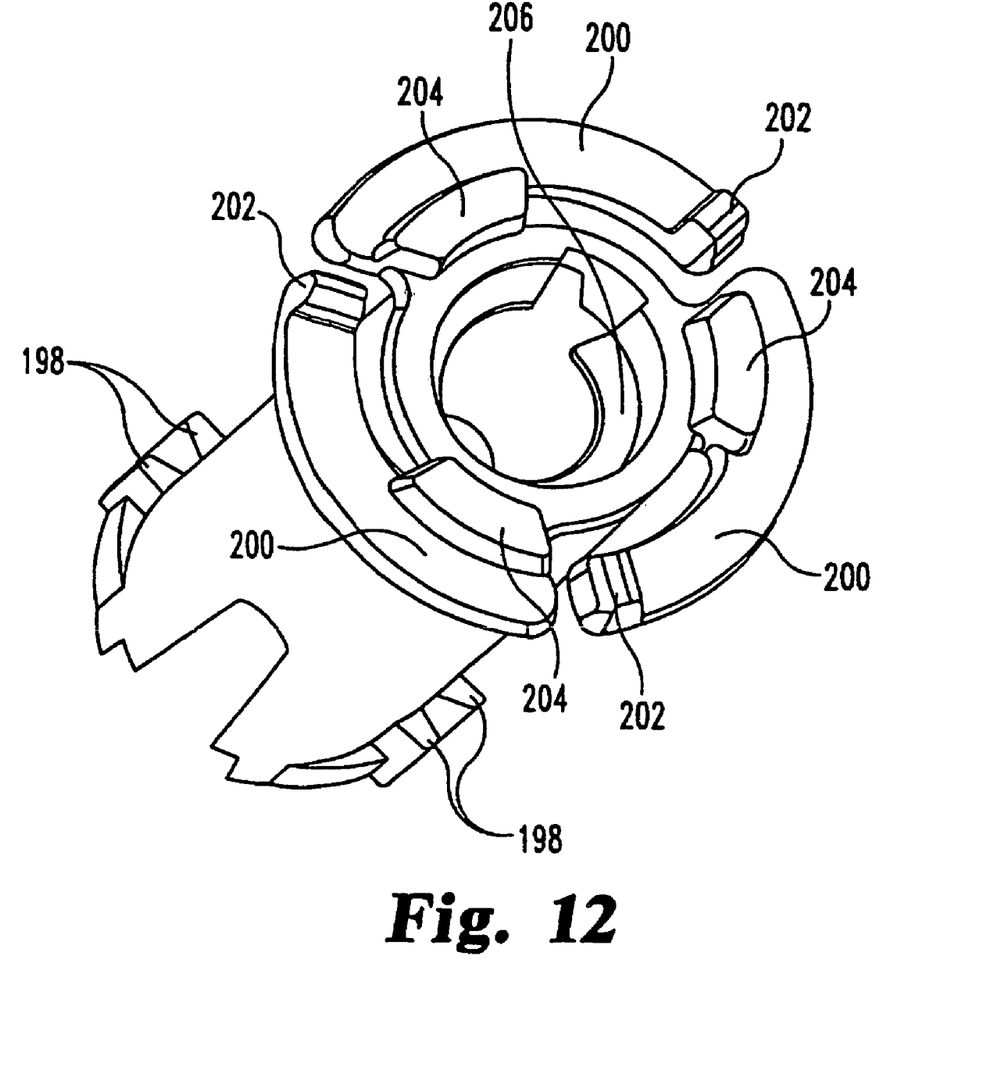
FIG. 12 is a perspective distal end view of the nut of FIG. 2.

As shown in FIGS. 2 and 3 and 12, nut 64 is injection molded in one piece from a resilient plastic and is generally cylindrical in shape. A pair of notches 192 axially extend from the proximal end of the nut body to form a pair of resilient proximal legs 194. Each leg 194 at it proximal end includes a raised, angled portion 196 and two axially extending splines 198 extending therefrom. One of the four splines 198 is slightly longer axially than the other three splines 198 to be the first guide into the nut driver splines. The angling of portion 196 aids in the nut driver initially camming legs 194 resiliently inward during assembly of the nut to the nut driver via the insertion of the proximal end of the nut therein, which legs 194 spring back to prevent removal of the nut therefrom when fully inserted. The distal region of nut 64 includes a series of arcuate leaf springs 200, such as three as shown, that are resilient in the axial direction and which extend from three flange segments 199 that are equally angularly spaced around and project from the exterior periphery of the nut body. The end of each spring 200 includes a ramp shaped tooth 202 that axially extends distally for engagement with ribs 104 of housing 60 to prevent inadvertent nut rotation when the nut is rotationally disengaged from the nut driver. Three elements 204 integrally formed with flange segments 199 axially project in the distal direction to directly contact housing shoulders 90, 94 when the end of an injection has been reached The interior surface of the distal region of nut 64 includes an internal helical threading 206. Threading 206 is a single start thread that extends about 350° of the circumference of nut 64.

Splines 198 of nut 64 are used in the selective engagement of nut 64 and driver 62. Splines 198 are adapted to interfit with a series of axially extending splines 189 shown in FIG. 4 arranged circumferentially about the inner surface of nut driver 62. Splines 189 are longitudinally disposed so as to have distal ends that end proximally of where tubular portion 180 meets reduced diameter portion 182. In the shown embodiment, eighteen splines 189 are provided such that each spline is 20 circumferential degrees apart from an adjacent spline, and such splines are in alignment with splines 186. The splines 189 and 198 are sized and positioned so as to not be in engagement for all axial arrangements of nut driver 62 relative to nut 64, but when engaged result in a rotational locking together of the nut driver and nut. While splines 198 and 189 cooperate to provide this locking function in the shown embodiment, other types of cooperating elements that achieve a selective rotational locking may be employed within the scope of the invention.

As shown in FIGS. 2 and 3, screw element 66 is formed in one piece from a lightweight material, such as injection molded plastic, and axially extends within the interior hollows of nut 64, nut driver 62 and housing 60. Screw element 66 includes a cylindrical shaft 210 that ends at a rectangular stem 211 that leads to an enlarged disc-shaped head 212, which head distributes force on the cartridge piston it advances during dispensing operations. A helical threading 214 protrudes from and extends along the axial length of shaft 210. Threading 214 includes a 90° bend at its proximal end that serves as a thread stop 216 to indicate to the user that there is an insufficient dosage of medication remaining in cartridge 40. Specifically, thread stop 216 is positioned such that during dose preparing, the abutment of the end of the nut threading 206 with thread stop 216 prevents additional proximal rotation of nut 64 to stop the user from dialing up the fixed dose when less than such a fixed dose remains in the cartridge. Stop 216 is also the entry key into the nut for assembly.

Axially extending grooves are provided on two opposing sides of shaft 210, and each includes a rack or row of transversely extending ratchet teeth 218 formed therein. A number of axially extending flats are shown within the center of various axial segments of the ratchet teeth and result from ejector blades in the mold to eject the part out of the tool during manufacture. The grooves with ratchet teeth 218 interrupt threading 214, and the row of ratchet teeth axially extend along the length of shaft 210 a distance at least as great as the entire length of travel of the screw element during the life of pen 20. Flange 96 and 100 fit within the shaft groove to rotabably lock screw element 66 within housing 60, and tangs 98 and 102 engage ratchet teeth 218 to allow axial distal movement while preventing proximal movement of the screw element 66 relative to the housing 60.

Near the proximal end, shaft 210 includes a cam-shaped rib 220 diameterically disposed from thread stop 216. During manufacturing assembly, screw element 66 is axially inserted proximally into nut 64, and nut threading 206 is resiliently cammed out by rib 220 and then snaps thereover to prevent removal of the screw element from the nut. A flow restrictor 222 through shaft 210 exists for proper plastic flow into the mold at injection.

The structure of injector pen 20 will be further understood in view of the following explanation of its operation. Initially, a user requiring the fixed dose of the contained medication will locate pen 20, which pen is typically in the arrangement shown in FIG. 1, which is the arrangement the pen is in immediately after an injection.

In order to prepare a dose for injection, it is first necessary to place nut driver 62 in a zero dose radial position relative to the housing. Assuming pen 20 is in the radial or angular position relative to housing 60 resulting from the previous injection, which position is shown in FIG. 1 as well as FIG. 7a and FIG. 7, pen 20 must be reset to the radial position associated with a zero dose by moving the driver 62 through the reset segment of the travel path. In particular, typically while clutching the housing 60 in one hand, a user manually grips grip portion 174 and then begins to spin the nut driver relative to both the housing 60 and the nut 64. The proper direction to spin nut driver 62 during reset is indicated by a visual cue in the form of an arrow 80a visible through window 78. Multiple arrows can be provided such that an arrow is always so visible during the reset spinning. During this spinning, follower 150 slides along guide rib portion 130, and the user is notified when the driver spinning, and thereby this driver resetting, is complete by the tactile notice made by housing finger 110 snapping over spline 182a, and additionally, by the abutment of follower surface 158 against guide region 136a that provides a physical stop at such reset position.

If instead of such a spinning the user disregards the instructional cue and attempts to spin nut driver 62 in the opposite direction, the abutment of follower surface 154 against guide region 138 provides a physical stop of such incorrect operation. If a user disregards the instructional cue and attempts to plunge driver 62 during the nut driver spinning, such motion is prevented by the distal face 63 of nut driver 62 abutting the nut 64 at flange segments 199 which in turn, via elements 204, abuts the housing shoulders 90 and 94. If a user disregards the instructional cue and attempts to pull driver 62 proximally during the nut driver spinning, such motion is inhibited by the reluctance of housing finger 112 from resiliently snapping over the flange 184, and further, after the reset spinning initially causes the follower 150 to enter the space below guide rib portion 130, by the abutment of follower surface 156 against the distal surface of guide rib portion 130.

Figure 8:
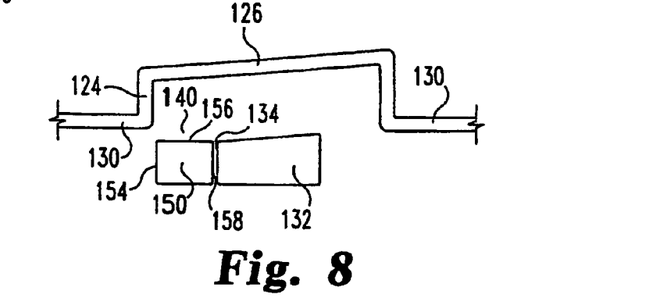
FIG. 8 is a two dimensional representation conceptually similar to FIG. 7, but wherein the apparatus is shown arranged after angular resetting is complete and prior to the apparatus being manipulated in the nut engaging phase of its operation.
Figure 8A:
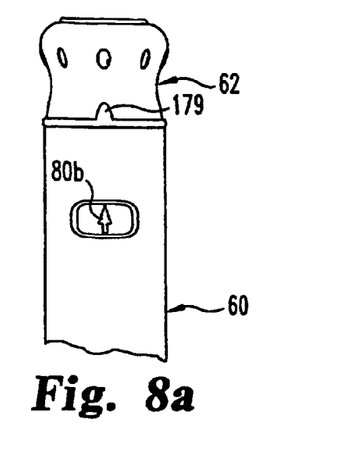
FIG. 8a is a front view of the proximal end of the apparatus when arranged as shown in FIG. 8.

After the driver 62 has been so moved to the end of the reset segment of the travel path, driver 62 is rotationally aligned with the nut engaging segment of its travel path, and pen 20 is arranged as shown in FIG. 8a and FIG. 8, with the proper direction for the user to then shift nut driver 62 indicated by a visual cue in the form of an arrow 80b visible through window 78. When a user then grips grip portion 174 and properly pulls nut driver 62 proximally with respect to housing 60 and nut 64 to move the nut driver through the nut engaging segment of the driver travel path, follower 150 slides along guide face portion 134 and guide rib portion 124, until the abutment of follower surface 156 against the distal surface of guide rib portion 126 that provides a physical stop at such position. As the driver so moves axially through the nut engaging segment of its travel path, splines 189 move axially from a position not in engagement with splines 198 to a position in engagement with splines 198, rotatably locking together driver 62 and nut 64. If after starting the travel of the driver 62 through the nut engagement segment of its travel path the user disregards the instructional cue and attempts to spin nut driver 62 in either direction, the abutment of either follower surface 158 or 154 against guide region 134 or a facing surface of guide rib portion 124, respectively, provides a physical stop of such incorrect operation.

Figure 9:
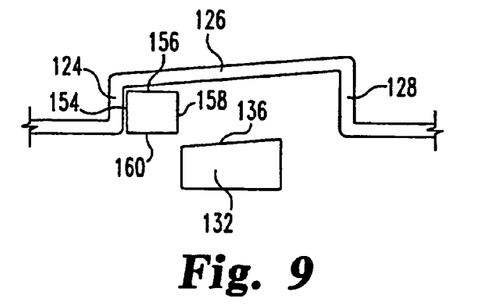
FIG. 9 is a two dimensional representation conceptually similar to FIG. 7, but wherein the apparatus is shown arranged after the nut engaging phase is complete and prior to the apparatus being manipulated in the nut rotating phase of its operation.
Figure 9A:
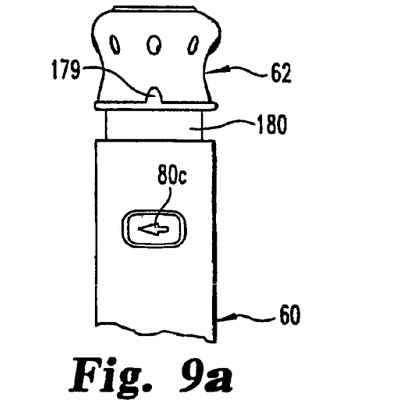
FIG. 9a is a front view of the proximal end of the apparatus when arranged as shown in FIG. 9.

After the driver 62 has been so moved to the end of the nut engaging segment, pen 20 is arranged as shown in FIG. 9a and FIG. 9, with the proper direction for the user to then screw nut driver 62 indicated by a visual cue in the form of an arrow 80c visible through window 78. When a user then grips grip portion 174 and screws nut driver 62 with respect to housing 60 to move the nut driver through the nut rotating segment of the driver travel path, follower 150 slides along guide rib portion 126 and guide face portion 136, until the abutment of follower surface 158 against the facing surface of guide rib portion 128 that provides a physical stop at such position, at which angular position dose delivery is possible. As the driver is so screwed proximally, the nut 64 rotatably locked therewith similarly rotates and screws proximally along the rotatably locked screw element 66, and further the sliding of splines 186 past finger 112 angularly locates the driver and provides audible clicks indicative of a working pen. If during the travel of the driver 62 through the nut rotating segment of its travel path the user disregards the instructional cue and attempts to further pull without rotation the nut driver 62 proximally, the abutment of follower surface 156 against the facing surface of guide rib portion 126 provides a physical stop of such incorrect operation. Still further, if a user after starting the nut driver screwing attempts to incorrectly plunge nut driver 62 prior to reaching the end of the nut engaging segment, the abutment of follower surface 160 against guide region 136 provides a physical stop of such incorrect operation, and thereby any dispensing of anything less than the full fixed dose is prevented.

Figure 10:
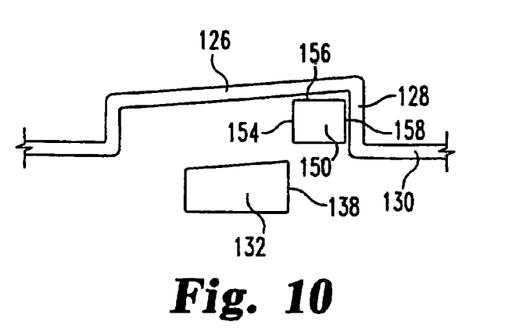
FIG. 10 is a two dimensional representation conceptually similar to FIG. 7, but wherein the apparatus is shown arranged after the nut rotating phase is complete, and prior to the apparatus being manipulated in the injecting phase of its operation.
Figure 10A:
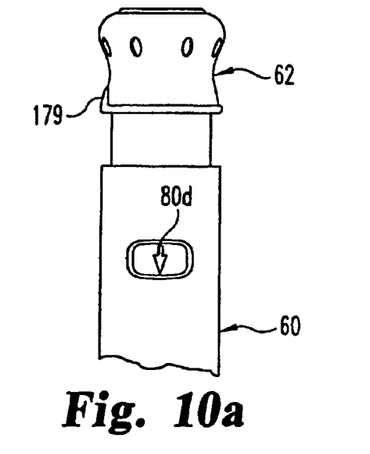
FIG. 10a is a front view of the proximal end of the apparatus when arranged as shown in FIG. 10.
Figure 11:
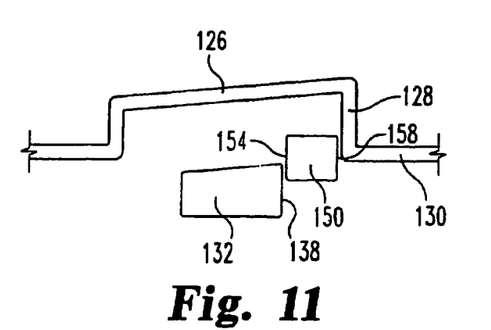
FIG. 11 is a two dimensional representation conceptually similar to FIG. 7, but wherein the apparatus is shown arranged during the injecting phase of its operation.
Figure 11A:
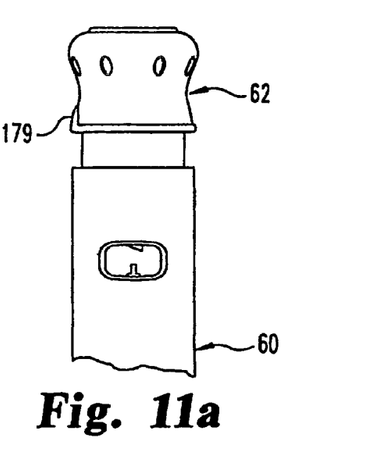

After the driver 62 has been so moved to the end of the nut rotating segment of the travel path, driver 62 is rotationally aligned with the injecting segment of its travel path, and pen 20 is arranged as shown in FIG. 10a and FIG. 10, with the proper direction for the user to then shift nut driver 62 indicated by a visual cue in the form of an arrow 80d visible through window 78. At this time, or at any other time during dose preparing, if the user elects not to administer a dose, the pen can be manipulated back into any prior arrangement that occurred after the prior injection, such as any position shown in FIGS. 7-9, without dispensing any medication.

If injection is still desired when pen 20 is arranged as shown in FIG. 10a, after the user ensures that pen needle assembly 50 is installed and exposed, pen 20 is manipulated such that injection needle distal tip 54 properly penetrates, for example, a user's skin, and an axial, distal plunging force is manually applied to proximal end 175 to force nut driver 62 distally toward the housing, such as with a thumb or index finger of the hand which grasps the housing. Initially during this nut driver plunging, nut driver 62 shifts distally through the injecting segment of the driver travel path, with follower 150 sliding along guide rib portion 128 and guide face 138, without motion of nut 64 to close up the axial gap between the distal face of nut driver 62 and nut flange segments 199. Then, when such gap is closed, continued distal motion of nut driver 62 shifts nut 64, and thereby screw element 66, distally and without rotation to advance cartridge piston 44 and force medication though the pen needle. Nut driver plunging, and thereby advancement of nut 64 and screw element 66, continues until nut elements 204 abut housing shoulder 90 and 94 to halt the injection, which halting is further indicated to the user by the audible click and tactile notice created by the housing finger 112 snapping over the shifting driver flange 184

If while follower 150 slides along guide rib portion 128 and guide face portion 138 during injecting the user attempts to spin nut driver 62 in either direction, the abutment of either follower surface 154 or 158 against guide region 138 or a facing surface of guide rib portion 128, respectively, provides a physical stop of such incorrect operation, thereby preventing a user from, for example, rotating the nut before the injection of the full dose is complete.

Figure 7:
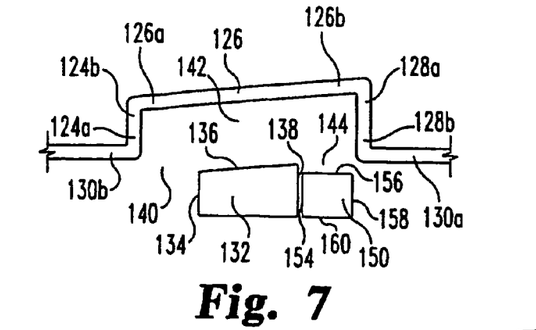
FIG. 7 is a two dimensional representation of portions of the guide and follower of the apparatus of FIG. 1, wherein the apparatus is shown arranged at an initial stage of dose preparing and as arranged immediately after the prior injection.
Figure 7A:
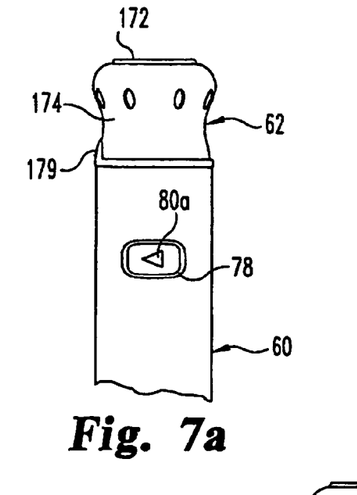
FIG. 7a is a front view of the proximal end of the apparatus when arranged as shown in FIG. 7.

At this point, nut driver 62 has returned to the same axial and rotational position relative to the housing at which it was disposed after completion of the prior injection, and which is shown in FIGS. 7 and 7a, and driver 62 is again rotatably free of nut 64 due to splines 189 having been moved axially out of engagement with splines 198 during travel of nut driver 62 through the injecting section of the travel path.

Pen 20 can continue to be used to deliver the fixed dose in the above described fashion until the medicine remaining in the cartridge is insufficient for a proper dosing. This insufficiency is indicated to a user by her inability to fully set the desired dose due to nut threading 206 abutting thread stop 216, at which time the nut and driver can not be rotated proximally any farther. When insufficient medicine remains, pen 20 is to be disposed of and replaced with a similar but entirely new pen.

In a not shown embodiment, the concept of the present invention may also be utilized in modifying an existing pen, such as disclosed in PCT Publication Number WO 02/30495, to better encourage correct operation of that pen. In such a modified pen, a guide and follower similar to rib 122 and follower 150 are provided on the housing and the dial, but such are provided in addition to the cooperating thread and fingers standard to the device, which thread is engaged by the fingers for less than 360° of travel during fixed dose setting. The follower and guide engagement sequences operation in a way that is not defeatable by an untimely operation of any portion of the dial assembly of the pen. The zero dose radial position stop, as well as a stop to prevent the pen dial from being inappropriately dialed while in the process of an injection, and optionally to stop it from being rotated, if desired within the priming phase of its operation, may be provided by separate islands similar to guide element 132.

While this invention has been shown and described as having various designs, the present invention may be modified within the spirit and scope of this disclosure. For example, if sufficient axial play was provided between the nut and nut driver when rotationally engaged, the helical orientation of guide rib 126 can be eliminated and such guide rib could merely be transversely arranged. Still further, the positions of the follower and guide on the nut driver and housing may be reversed in an alternate embodiment. This application is therefore intended to cover any variations, uses or adaptations of the invention using its general principles. Further, this application is intended to cover such departures from the present disclosure as come within known or customary practice in the art to which this invention pertains.

We claim:

1. A medication dispensing apparatus comprising:

a housing;

an axially extending screw element rotatably and axially fixed within said housing during dose preparing, and rotatably fixed and axially movable in a distal direction relative to said housing during dose injecting, said screw element including a threaded shaft;

a fluid container defining a medicine-filled reservoir with a movable piston at one end and an outlet at the other end, said piston engagable by said screw element to be advanced toward said outlet when said screw element is moved distally;

a nut threadedly engaged with the screw element shaft to be axially movable relative thereto during rotation of said nut relative to said screw element;

a nut driver rotatably and axially shiftable relative to said housing;

wherein said nut and said nut driver include cooperating elements which when engaged rotatably lock together said nut and said nut driver, and which when disengaged permit relative rotation of said nut and said nut driver;

a guide disposed on one of said nut driver and said housing;

a follower disposed on the other of said nut driver and said housing;

wherein said guide and follower comprise a surface abutting relationship to promote a user moving said nut driver relative to said housing along a travel path that operates the apparatus, said travel path including a dose preparing section and a dose injecting section, said dose preparing section including a reset segment, a nut engaging segment, and a nut rotating segment connected in sequence, and wherein said injecting section connects said nut rotating segment with said reset segment;

wherein said cooperating elements of said nut and said nut driver are disengaged when said nut driver is disposed in said reset segment;

wherein said cooperating elements of said nut and said nut driver become engaged when said nut driver is shifted through said nut engaging segment from said reset segment to said nut rotating segment;

wherein the engagement of said cooperating elements of said nut and said nut driver cause said nut to screw proximally along said threaded shaft when said nut driver is shifted through said nut rotating segment from said nut engaging segment to said injecting section;

wherein when said nut driver is shifted through said injecting section from said nut rotating segment to said reset segment, said nut and said screw element are shifted in the distal direction to axially advance said fluid container piston to dispense medicine from said outlet, and said cooperating elements of said nut and said nut driver become disengaged; and said guide including a hard stop for said follower to define an end of said reset segment of said travel path, and said hard stop when abutted by said follower rotationally aligns said nut driver with said nut engaging segment of said travel path, wherein along said injecting section of said travel path, said guide comprises first and second surfaces that define a channel in which said follower is slidable, said surfaces during injecting serving as physical stops to prevent rotation of said nut driver by abutment by said follower until an injection is complete, wherein along said nut rotating segment of said travel path, said guide comprises third and fourth surfaces that define a channel in which said follower is slidable, said third surface providing a distal barrier during nut rotating that prevents distal plunging of said nut driver by abutment by said follower until said follower passes from said nut engaging segment to said injecting section, thereby limiting misuse of the apparatus.

2. The medication dispensing apparatus of claim 1 wherein said nut engaging segment and said dose injecting section of said travel path are oriented in the axial direction.

3. The medication dispensing apparatus of claim 1 wherein said reset segment of said travel path is oriented generally transverse to said axial direction.

4. The medication dispensing apparatus of claim 1 wherein said nut rotating segment of said travel path is helically oriented.

5. The medication dispensing apparatus of claim 1 wherein said travel path involves both 360 degrees of rotation of said nut driver and an equal amount of distal and proximal travel of said nut driver, whereby said nut driver, at the end of an injection, has the same axial position and same rotational position as at the end of the prior injection, and wherein said guide includes a second hard stop for said follower to define a second end of said reset segment of said travel path, which second hard stop prevents rotation of said nut driver in one direction after the end of the injection by abutment by said follower.

6. The medication dispensing apparatus of claim 1 wherein said follower comprises an outward projection formed on said nut driver, said outward projection being radially fixed at all times during pen use.

7. The medication dispensing apparatus of claim 6 wherein said guide comprises a projecting rib formed on said housing and that extends continuously around an interior surface of said housing.

* * * * *

UNITED STATES PATENT AND TRADEMARK OFFICE
CERTIFICATE OF CORRECTION

PATENT NO. : 7,695,454 B2  Page 1 of 1
APPLICATION NO. : 10/575502
DATED : April 13, 2010
INVENTOR(S) : Traci Jo Barron, Andrew Christopher Burroughs and David William Hixson

It is certified that error appears in the above-identified patent and that said Letters Patent is hereby corrected as shown below:

On the Title page:
Insert -- [60] Related U.S. Application Data
Provisional application No. 60/511,735, filed on October 16, 2003 --

On the first page of the specification, insert the following cross-reference after the title:
-- This is the national phase application, under 35 USC 371,
for PCT/US2004/032304, filed 15 October 2004 (15.10.2004), which
claims the benefit, under 35 USC 119(e), of US provisional
application 60/511,735, filed 16 October 2003. --

Signed and Sealed this

Sixth Day of July, 2010

David J. Kappos
*Director of the United States Patent and Trademark Office*